(12) United States Patent
Swaney et al.

(10) Patent No.: US 11,738,102 B2
(45) Date of Patent: *Aug. 29, 2023

(54) INSTRUMENT STERILIZATION DEVICE (71) Applicant: Hai Solutions, Inc., Carlsbad, CA (US)

(72) Inventors: Paul Swaney, Carlsbad, CA (US); Nicholas Perrenoud, Carlsbad, CA (US); Adnan Abbas, Carlsbad, CA (US)

(73) Assignee: HAI Solutions, Inc., Carlsbad, CA (US)

( * ) Notice: Subject to any disclaimer, the term of this patent is extended or adjusted under 35 U.S.C. 154(b) by 458 days.

This patent is subject to a terminal disclaimer.

(21) Appl. No.: 16/788,137

(22) Filed: Feb. 11, 2020

(65) Prior Publication Data

US 2020/0254121 A1 Aug. 13, 2020

(51) Int. Cl.
A61L 2/10 (2006.01)

(52) U.S. Cl.
CPC ............. *A61L 2/10* (2013.01); *A61L 2202/24* (2013.01)

(58) Field of Classification Search
CPC .... A61L 2/10; A61L 2202/24; A61L 2202/11; A61L 2202/122
See application file for complete search history.

(56) References Cited

U.S. PATENT DOCUMENTS

| | | | |
|---|---|---|---|
| 7,390,417 B2 | 6/2008 | Kuhlmann et al. | |
| 8,633,454 B2 | 1/2014 | Durkin | |
| 9,764,126 B2 | 9/2017 | Tornblom | |
| 10,610,609 B2 | 4/2020 | Swaney et al. | |
| 2003/0017073 A1* | 1/2003 | Eckhardt | A61L 2/10 422/24 |
| 2004/0034398 A1 | 2/2004 | Eckhardt et al. | |
| 2004/0200783 A1 | 10/2004 | Castellini | |
| 2007/0176117 A1 | 8/2007 | Redmond et al. | |
| 2007/0295213 A1 | 12/2007 | Okamoto et al. | |
| 2008/0208297 A1 | 8/2008 | Gertner et al. | |
| 2009/0117001 A1 | 5/2009 | Hyde et al. | |
| 2009/0314956 A1* | 12/2009 | Long | A61L 2/10 250/455.11 |
| 2011/0085936 A1* | 4/2011 | Haytman | A61L 2/084 250/492.1 |
| 2011/0104017 A1 | 5/2011 | Migliore et al. | |
| 2012/0321509 A1 | 12/2012 | Bak | |
| 2013/0004479 A1 | 1/2013 | DiCosimo et al. | |

(Continued)

FOREIGN PATENT DOCUMENTS

| | | |
|---|---|---|
| CN | 202724294 U | 2/2013 |
| CN | 104815823 A | 8/2015 |

(Continued)

OTHER PUBLICATIONS

International Search Report and Written Opinion dated Mar. 28, 2019 for International Application Serial No. PCT/US2018/057138 filed on Oct. 23, 2018.

(Continued)

*Primary Examiner* — Regina M Yoo (74) *Attorney, Agent, or Firm* — K&L Gates LLP; Brian J. Novak; Giorgios N. Kefallinos (57) ABSTRACT Described herein generally are sterilization devices that can allow sterilization of surface(s) of instrument(s). Methods of using these devices are also described.

14 Claims, 6 Drawing Sheets

(56) References Cited

U.S. PATENT DOCUMENTS

| | | | |
|---|---|---|---|
| 2013/0045133 A1* | 2/2013 | Maguire | A61L 2/24 422/1 |
| 2013/0323119 A1 | 12/2013 | Alwan et al. | |
| 2013/0323120 A1 | 12/2013 | Ma | |
| 2013/0336839 A1* | 12/2013 | Gil | A61L 2/10 422/107 |
| 2014/0038305 A1 | 2/2014 | Sharavara et al. | |
| 2014/0305470 A1* | 10/2014 | Desu-Kalyanam | A61L 2/10 15/36 |
| 2015/0290347 A1 | 10/2015 | Braden et al. | |
| 2016/0324997 A1 | 11/2016 | Dayton | |
| 2017/0136136 A1 | 5/2017 | Li et al. | |
| 2017/0165386 A1* | 6/2017 | Huang | A61L 2/26 |
| 2017/0232123 A1* | 8/2017 | Burapachaisri | A61M 39/10 422/24 |
| 2018/0169286 A1 | 6/2018 | Henniges et al. | |
| 2018/0290900 A1 | 10/2018 | Lu et al. | |
| 2018/0296709 A1 | 10/2018 | Mishkin et al. | |
| 2018/0361001 A1 | 12/2018 | Liao et al. | |
| 2019/0201563 A1* | 7/2019 | Swaney | A61L 2/28 |
| 2019/0381202 A1* | 12/2019 | Pedrazzi | A61L 2/26 |
| 2021/0023247 A1 | 1/2021 | Swaney et al. | |

FOREIGN PATENT DOCUMENTS

| | | | |
|---|---|---|---|
| JP | 3459831 B2 * | 10/2003 | A61B 1/00059 |
| JP | 2011016074 A | 1/2011 | |
| RU | 111976 U1 | 1/2012 | |
| TW | 201827112 A | 8/2018 | |
| WO | WO-2014021921 A2 * | 2/2014 | A61C 19/002 |
| WO | 2014/202401 A1 | 12/2014 | |
| WO | WO-2015157662 A1 * | 10/2015 | A61L 2/10 |
| WO | 2017/062260 A2 | 4/2017 | |
| WO | 2019/084029 A1 | 5/2019 | |
| WO | 2020/167843 A1 | 8/2020 | |
| WO | 2020/167847 A1 | 8/2020 | |
| WO | 2020/167850 A1 | 8/2020 | |

OTHER PUBLICATIONS

Extended European Search Report, dated Jun. 14, 2021, for European Application No. 18870694.9.

Solid-State Lighting, 2013, pp. 1-24, URL:https://microem.ru/files/2014/03/16.10.2013 pdf (XP055697168) [Translation not readily available].

International Search Report and Written Opinion dated Apr. 29, 2020 for International Application Serial No. PCT/US20/017763 filed on Feb. 11, 2020.

Inolux, IN-C39ATK/IN-C39BTK/ IN-C39CTK UVC Series 3939 UVC LED, <URL:https://www.mouser.jp/datasheet/2/180/IN-C39(X)TK_UVC_Series_ V1 .1-1625669.pdf> (Oct. 31, 2018).

Foxx Life Sciences, Autofil Sterile Disposable Vacuum Bottle Top Filters with 0.2um Sterilizing PES Membrane, 500mL, 24/CS,<URL:https://www.amazon.com/Autofil-Sterile-Disposable-Sterilizing-Membrane/dp/B00HSDSRHA#feature-bullets-btf>(Mar. 14, 2017).

International Search Report and Written Opinion dated Apr. 23, 2020 for International Application Serial No. PCT/US2020/017767 filed on Feb. 11, 2020.

International Search Report dated Jun. 15, 2020 for International Application Serial No. PCT/US2020/017771 filed on Feb. 11, 2020.

U.S. Appl. No. 17/429,910, filed Aug. 10, 2021.

U.S. Appl. No. 17/429,916, filed Aug. 10, 2021.

* cited by examiner

INSTRUMENT STERILIZATION DEVICE

CROSS REFERENCE TO RELATED APPLICATION

This application claims the benefit of U.S. Provisional Patent Application No. 62/804,065, filed Feb. 11, 2019, the entire disclosure which is incorporated herein by reference.

FIELD

The present invention relates generally to sterilization devices.

SUMMARY

Described herein generally are sterilization devices that can allow a, physician, nurse, assistant, caregiver, provider, or the like to disinfect surfaces of instruments during normal and routine medical care. Also, described herein are the methods for using the sterilization devices.

The described sterilization devices can include a body and an adapter. In some embodiments, the body can include an activation or on/off switch, at least one indicator light, at least one battery, and a light source.

In some embodiments, the body can include an activation or on/off switch, at least one indicator light, a power source, and a light source.

In other embodiments, the body can optionally include a printed circuit board including a processor and memory.

In yet other embodiments, the devices described herein can have independent drivers that do not require a processor. In some embodiments, the independent drivers are LED drivers. In some embodiments, the adapter can be a mold or shell.

In some embodiments, the adapter can be biocompatible. In other embodiments the adapter can be disposable. In some embodiments the adapter can be an instrument mold. In other embodiments, the adapter can be a shell or body. In some embodiments, the instrument mold can be freely independent of the body of the device. In other embodiments, the shell can be interchangeable with other shells or bodies.

In some embodiments, the devices can be small, lightweight, and/or handheld. However, the devices need not be small, lightweight, and/or handheld and can include a body that is virtually any size or weight.

In some embodiments, the devices can deliver ultraviolet light to sterilize an instrument surface(s). In some embodiments, the ultraviolet light can be ultraviolet C (UVC) light. In other embodiments, the ultraviolet light can be ultraviolet B light.

In one embodiment, the devices can deliver UVC light from a 3.5 mm×3.5 mm light-emitting diode (LED) with a 275 nm wavelength fora 5-10 second interval.

The devices described can effectively denature any microbe or cellular structure on any surface of an instrument.

In some embodiments, the devices can sterilize the instrument surface(s) within or in less than about 5 seconds. In other embodiments, the devices can sterilize the instrument surface(s) within or in less than about 10 seconds.

In some embodiments, the optical power from the LED can be about 10 mW. In other embodiments, the optical power from the LED can be up to 50 mW.

In other embodiments, the device can use only about 6 volts of power. In one embodiment, the device can use 3 volts of power, about 3 volts of power, or at least 3 volts of power.

In other embodiments, the devices can have a switch that activates the device to start sterilizing. In some embodiments, the devices can have an auto mode wherein the device begins to sterilize as soon as a connection is completed. In some embodiments, the device can have a multi-sensor. In other embodiments, the device can have at least one or more sensors.

In other embodiments, the device can have one or more indicator light(s) that can turn green once sterilization is complete. In some embodiments, the device can have one or more indicator light(s) which are blue and turn green once sterilization is complete. In other embodiments, the indicator light(s) can be, but are not limited to, red, blue, purple, yellow, no color, or orange, which then turn green upon completion of sterilization. In some embodiments, there can be a chromatic scheme. In other embodiments, the indicator light(s) are part of the adapter.

In other embodiments, the device can have a tactile response to indicate sterilization is complete. In some embodiments, the tactile response is vibration.

In some embodiments, the devices can sterilize the intended surface at a distance of about 1 mm to about 10 mm from the intended surface. In some embodiments, the distance is less than about 10 mm. In other embodiments, the distance is greater than about 1 mm.

Methods are also described for using the herein described devices. Methods can include connecting the devices to the adapters to sterilize the surface within about 5 seconds.

In other embodiments, the methods can include connecting the devices to several adapters and sterilizing sequentially one at a time or at the same time. Such sterilization for 1 to 20 adapters can take about 30 to about 40 seconds. In other embodiments, methods can include sterilization of 1 to 50 adapters.

In other embodiments, the devices described herein can include an inter-locking circuit. In some embodiments, the inter-locking circuit can be connected to the adaptor or to the shell to turn on the safety feature. In other embodiments, the inter-locking circuit can have an RFID chip or optical sensor configured to allow the adaptor and device to communicate. In some embodiments, the adaptor and device can communicate via physical, mechanical, or optical communication.

In some embodiments, the sterilization device described herein can comprise a body comprising at least one indicator light, a battery, and a light source; and an adapter. In other embodiments, the adapter is a body or shell configured to an instrument.

In other embodiments, the sterilization device described herein can comprise a body comprising at least one indicator light, a power source, and at least light source; and an adapter. In some embodiments, the adapter is a body or shell configured to an instrument for sterilization.

In some embodiments, a method of sterilization comprises inserting an instrument into a sterilization device to apply sterilizing light to the instrument. In other embodiments, the device sterilizes the surface of the instrument through the adapter shell.

DETAILED DESCRIPTION

Figure 1:
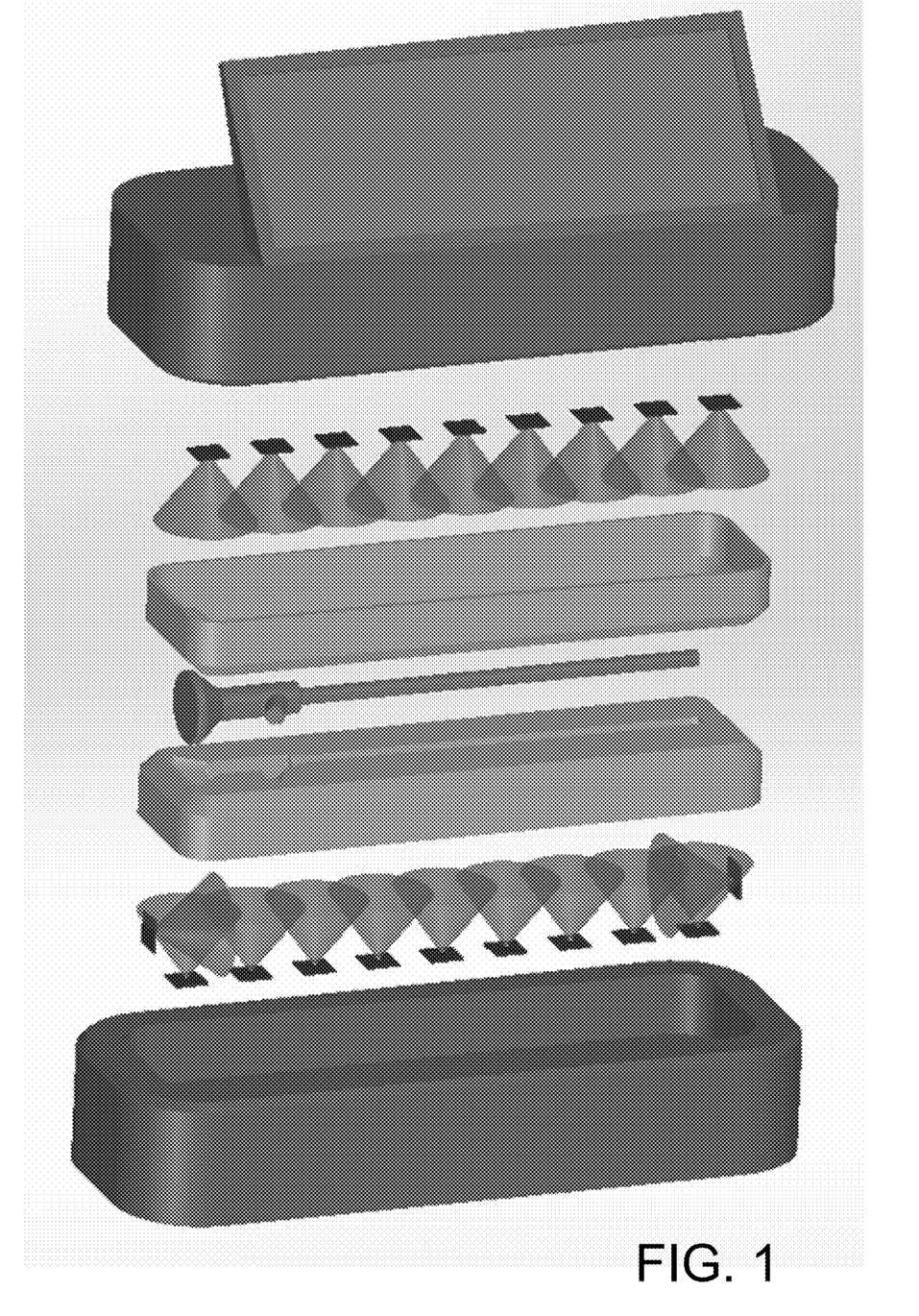
FIG. 1 illustrates an example embodiment of a device as described herein.
Figure 2:
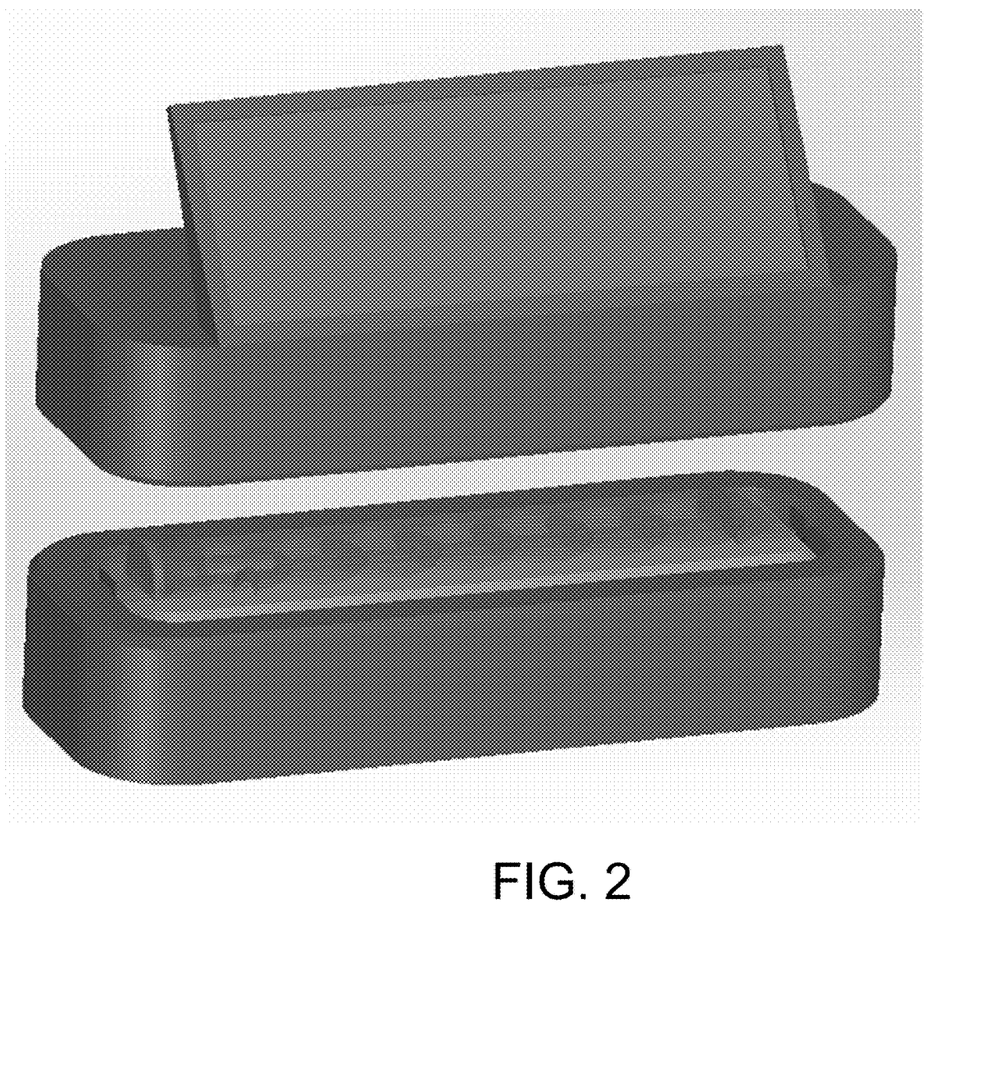
FIG. 2 illustrates an example embodiment of a device as described herein.
Figure 3:
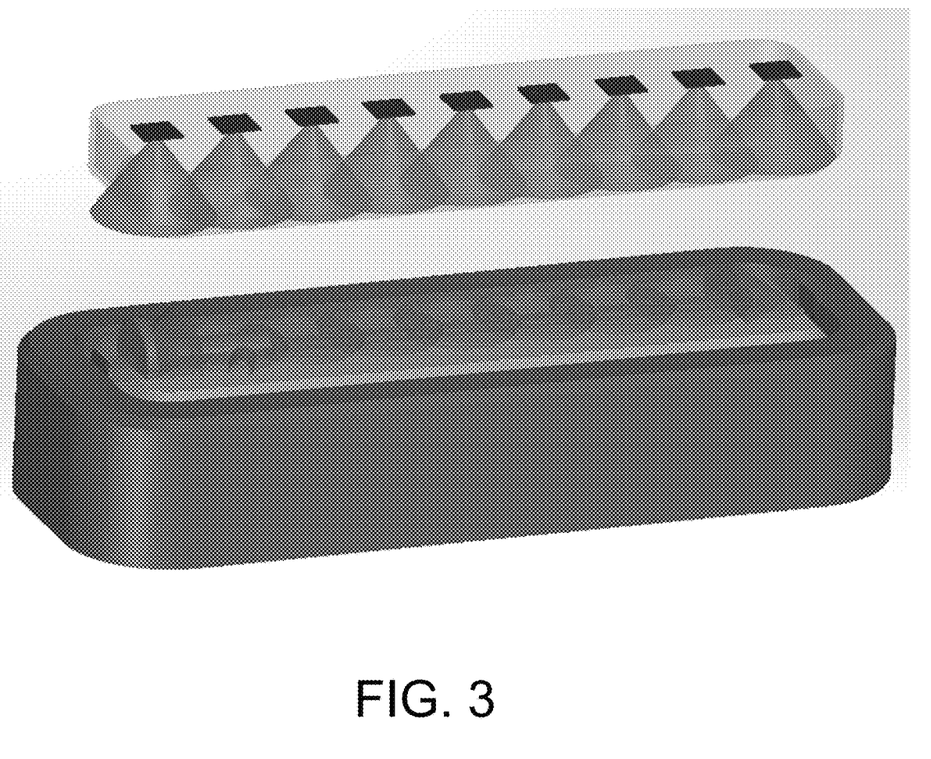
FIG. 3 illustrates an example embodiment of a device as described herein.
Figure 4:
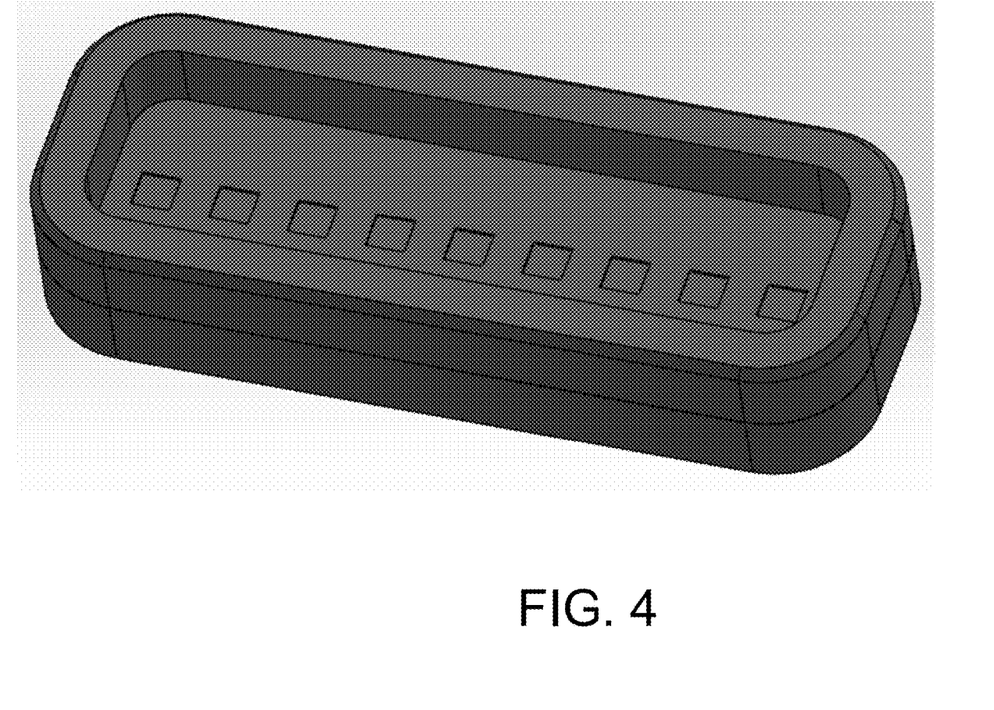
FIG. 4 illustrates an example embodiment of a device as described herein.
Figure 5:
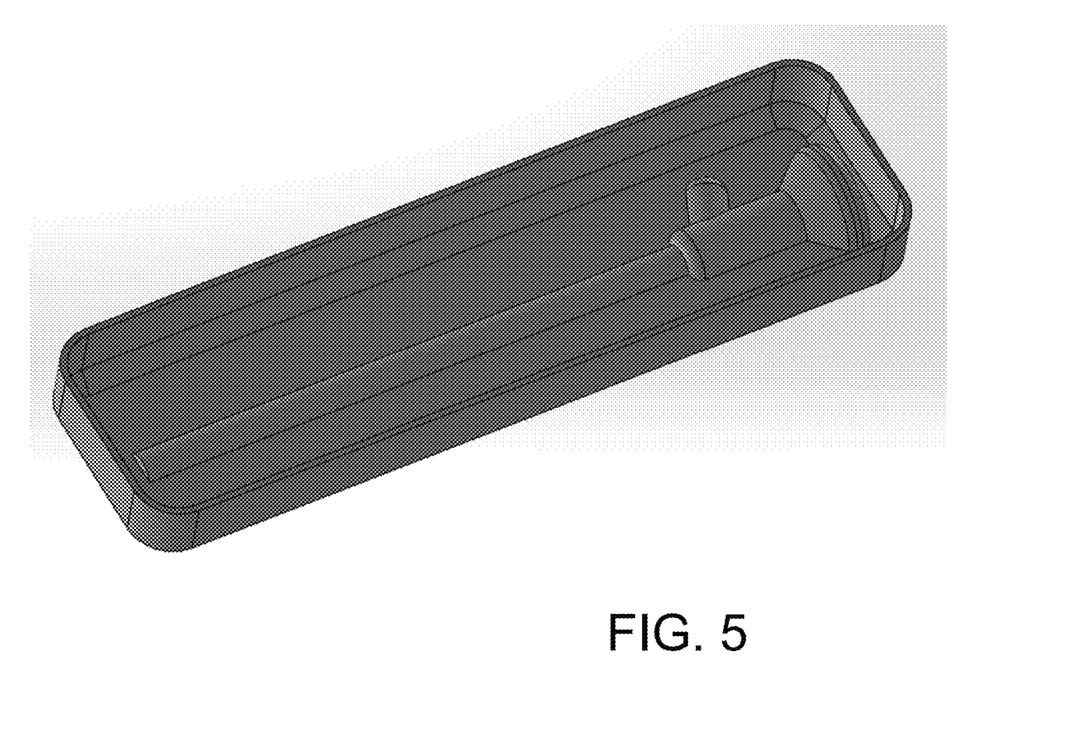
FIG. 5 illustrates an example embodiment of a device as described herein.
Figure 6:
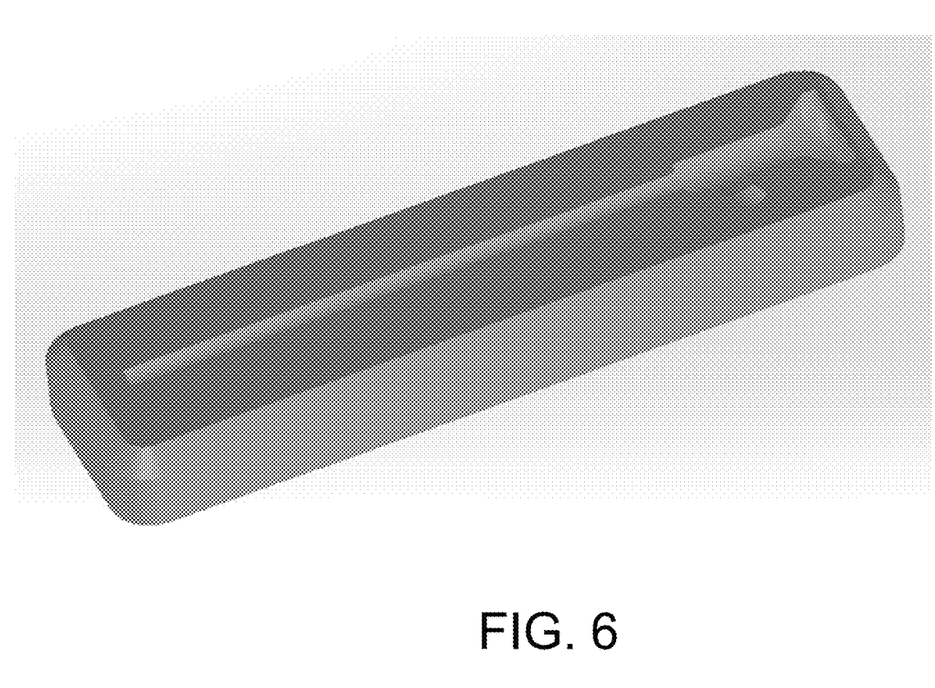
FIG. 6 illustrates an example embodiment of a device as described herein.

Described herein generally are devices that can reduce, eliminate, and/or prevent chances of infection.

In some embodiments, the devices are sterilization devices utilized for sterilization of the surfaces of instruments or medical tools.

Sterilization of the surface of these types of instruments can be very time consuming. In some instances, an instrument may require 1 to 20 treatments per month. Sterilization using the described devices can reduce this time burden, in some cases by about 66%.

Catheter and IV related bloodstream infections are common, and are primarily caused by microbial ingress, whether via airborne route or gross contact contamination, through a surface entry of the IV connector or via an access point around the venous catheter insertion. As previously described, the Center for Disease and Control (CDC) and Joint Commission recommend scrubbing a port for at least 15 seconds with an isopropyl pad in order to properly sterilize that port. This very time consuming and tedious sterilization process is thought to disinfect the surface of a port allowing the safe administration of fluids.

Due to time constraints, staff changes, and nursing irregularities, proper care is a consistent problem and contributing factor to healthcare acquired infections (HAI) known as CRBSI/CLBSI, catheter-related/central line bloodstream infections. Thus, there is a need in the field for an efficient time saving device to disinfect a surface/surfaces of an instrument/instruments.

Microbial contamination is an ongoing problem with instrumentation. Companies have provided methods for disinfecting. However, these devices require longer disinfecting times, e.g., greater than 1 min, cost more than the present devices, and have inconsistent disinfecting results.

In some embodiments, the devices are utilized for sterilization of endoscopes, working channels, luminal surfaces or borescopes.

In other embodiments, the instruments can be flexible or rigid.

Endoscopes are instruments which can be inserted in the human body allowing the physician to gain visualization via a camera system. Endoscopes also contain working channels allowing the physician to advance working instruments required to deliver treatment during a medical procedure. Endoscopes are utilized during a variety of procedures including ENT, General and Gastroenterology procedures. During these procedures working channels can accumulate contaminates like patient debris, tissue and bodily fluids like blood. If not properly decontaminated endoscopes can also transfer or transmit bacteria, microbes or other types of contamination. Serious or life threatening infections and or death can result due to a lack of decontamination or sterilization.

In some embodiments the adapter can utilize a longer disposable extension to deliver UVC light throughout the working channel(s) thereby irradiating, and sterilizing parts or sections of the endoscopes.

The present devices can sterilize instrument(s) quicker and more efficiently than even the present standards outline. The present devices can provide clinical benefits that enhance provider efficiency, and improve clinical outcomes while delivering significant cost savings. In some embodiments, the present devices can be built on a device/disposable platform that can deliver complete sterilization and at least a 4-log (99.99%) microbial reduction. This 4-log (99.99%) microbial reduction is greater than standard methods which only promise to deliver disinfection. In other embodiments the microbial reduction can be about a 4-log microbial reduction, about a 5-log microbial reduction, about a 6-log microbial reduction, about a 7-log microbial reduction, about a 8-log microbial reduction, at least about a 4-log microbial reduction, at least about a 5-log microbial reduction, at least about a 6-log microbial reduction, at least about a 7-log microbial reduction, at least about a 8-log microbial reduction, more than a 4-log microbial reduction, more than a 5-log microbial reduction, more than a 6-log microbial reduction, more than a 7-log microbial reduction, more than a 8-log microbial reduction, or between about a 4-log microbial reduction to about a 8-log microbial reduction.

The devices described herein can reduce methicillin-resistant *Staphylococcus aureus* (MSRA) bacteria on IV connectors with 99.99% kill after 1 second, 99.999% kill after 3 seconds, and >99.99999% after 7 seconds of UV light exposure. These results demonstrate the effectiveness of the devices described herein. In comparison, current methods on the market take days to reach only a 98% kill, whereas the devices described herein take a second to achieve a 99.99% kill.

In some embodiments, the devices described herein can be used to sterilize surfaces, spaces, orifices, or cavities. A patient as used herein can be a mammal such as a humans, horses, camels, dogs, cats, cows, bears, rodents, oxen, bison, buffalo, caribou, moose, deer, elk, sheep, goats, pigs, rabbits, pouched mammals, primates, carnivores, and the like. When used with/for patients, the devices can meet the highest safety standards imposed by local, regional, or governmental regulations for sterilization protocols.

The Center for Disease Control and Joint Commission sterilization protocols include scrubbing an IV connector engagements/surfaces with an isopropyl pad for 15 seconds. The devices described herein can reduce sterilization time when compared to the times set by the CDC and the Joint Commission. The present devices can sterilize connection ports in less than about 10 seconds or less than about 5 seconds. Thus, the present devices can save time when sterilizing.

One embodiment of a device as described herein can include a body. The body can be formed of non-conductive materials such as polymers. Exemplary polymers include, but are not limited to polyurethanes, silicones, polyesters such as polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; carboxymethyl cellulose; synthetic and natural rubbers such as polysiloxanes, latex, polymerized isoprene, bromo isobutylene isoprene, chloro isobutylene isoprene, polychloroprene, chlorosulphonated polyethylene, ethylene propylene, ethylene propylene diene monomer, fluoro silicone, hydrogenated nitrile butadiene, polyisoprene, isobutylene isoprene butyl, methyl vinyl silicone, acrylonitrile butadiene, acrylonitrile butadiene carboxy monomer, styrene butadiene, epichlorodydrin; and combinations thereof.

In some embodiments, body 102 can be formed of cyclic olefin copolymers. In other embodiments, body 102 can be formed of TOPAS®. TOPAS can be used to allow for at least 80% of the UV light to penetrate through it. Many other plastics/polymers will not allow for at least 80% of the UV light to penetrate through it.

The polymer or combination of polymers chosen to form the body can be rigid enough to hold a particular configuration and perform its intended function. In some embodiments, the polymer used is a thermal set rigid plastic. In other embodiments, the polymer is a flexible nylon or rubber polymer.

The body can include or be connected to an adapter. In some embodiments, the adapter can be sterile. In other embodiments, the adapter can be biocompatible. In some embodiments, the adapter can be disposable. In other embodiments the adapter can be reusable.

In some embodiments, the adapter cap can include a fiber optic extension or fiber. In other embodiments, the length of the extension can be about 1-2 inch(es) but could be up to about 1 foot, 2 ft, 3, ft, 4 ft, 5 ft, 6 ft or any length needed to delivery targeted therapy.

In some embodiments the adapter allows for UVC light to be coherent. In other embodiments the adapter can collimate the light in such a manner as to allow it to be distributed, delivered or magnified to the tip or end of the fiber optic fiber at maximum power.

In some embodiments, the adapter can be rigid, malleable or flexible. In other embodiments, the adapter can allow the user to control the orientation, shape or direction of the UV light.

In some embodiments, the adapter can be threaded to accept a threaded connection port. In other embodiments, the adapter may not be threaded so that it can be friction fitted to a connection port. In some embodiments, the adapter can magnetically fit with the connection port. In other embodiments, the device can include a circular recess so that any type of adapter can fit in it.

In some embodiments, the adapter can include a silica lens to allow ultraviolet light to penetrate and sterilize.

The body can include an activation or on/off switch. The switch can be a push button, a press button, or a toggle button/switch.

In other embodiments, the body may not include a switch. In such an embodiment, the body can include an auto mode wherein the device begins to sterilize as soon as a connection is completed. In some embodiments, the device can have at least one or more sensors. In other embodiments, the device can have multi-sensors. In some embodiments, the at least one or more sensors can be located anywhere on the device. In other embodiments, the multi-sensors can be located anywhere on the device. In some embodiments, the at least one or more sensors are configured to allow the device to begin sterilization upon the connection between the device and connection port. In other embodiments, the multi-sensors are configured to allow the device to begin sterilization upon the connection between the device and connection port.

A device can include at least one indicator light. The body can include six indicator lights. Indicator light(s) can be one color prior. In other embodiments, the indicator light(s) can turn red after the adapter is inserted into a connection port when the light(s) can change color indicating a sufficient connection. In some embodiments, when an instrument has been properly sterilized the indicator light(s) can change color. The indicator light(s) signal to a user that the instrument is sterilized and the adapter can be removed. In some embodiments, once the adapter is removed, the indicator lights can turn off. In other embodiments, the switch is pushed to power off the device.

The indicator lights on the body can progressively illuminate, for example the light adjacent to the switch to the light adjacent to the adapter cap. This progression can display the sterilization process time.

As described, different light color combinations can be used to indicate device status. In some embodiments, red light can indicate a port that is not sterilized and green light can indicate proper sterilization. In some embodiments, a blue light can be used to indicate in process. In some embodiments, only a single light is needed to provide status. In other embodiments, multiple lights can be used to provide status.

In some embodiments, there can be a chromatic scheme. In other embodiments, the indicator lights can be part of the adapter. In other embodiments, indicator lights can be located anywhere on the device. In some embodiments, the chromatic scheme can be used to determine the status of the sterilization. In other embodiments, the chromatic scheme can include blue light(s) which indicate the device has not yet been sterilized. In some embodiments, the chromatic scheme can include green light(s) which indicate the device has been sterilized. In other embodiments, the chromatic scheme can include red light(s) or orange light(s) which indicate the device has not been sterilized. In some embodiments, the chromatic scheme can include blue light(s) which indicate that the device has been sterilized.

In some embodiments, there is a substrate or liquid situated in a base of the adapter which can change colors at specific wavelengths. In other embodiments, the substrate or liquid can be clear and turn green upon completion of sterilization. In some embodiments, when the adapter is exposed to UV light the substrate will change. Once the substrate changes color it can be irreversible so that the adapter is single use and cannot be used again.

The body can house a power source. In some embodiments, the body can house at least one power source. The power source can be a battery, a plug, a plug connected to or plugged into a wall, or a combination thereof.

The body can house at least one battery. The body can optionally include a printed circuit board including at least one processor and memory. The battery can be any standard sized battery. Standard size batteries can include, but are not limited to round, cylindrical batteries such as AA, AAA, AAAA, C, D, and button cell (such as lithium button), coin cell, and non-round batteries such as box batteries, and the like. In still other embodiments, proprietary battery packs can be provided to fit a particular slot or opening on or in a device. In some embodiments, the device uses a battery providing about 1 volt, about 2 volts, about 3 volts, about 4 volts of power, about 5 volts of power, about 6 volts of power, about 7 volts of power, about 8 volts of power, about 9 volts of power, about 10 volts of power, about 11 volts of power, about 12 volts of power, at least about 4 volts of power, at least about 5 volts of power, at least about 6 volts of power, at least about 7 volts of power, at least about 8 volts of power, at least about 9 volts of power, at least about 10 volts of power, at least about 11 volts of power, at least about 12 volts of power, more than about 4 volts of power, more than about 5 volts of power, more than about 6 volts of power, more than about 7 volts of power, more than about 8 volts of power, more than about 9 volts of power, more than about 10 volts of power, more than about 11 volts of power, more than about 12 volts of power, between about 4 volts of power to about 11 volts of power, or between about 4 volts of power to about 12 volts of power.

In some embodiments, two voltages are provided. Either voltage can be about 9 volts of power, about 9.5 volts of power, about 10 volts of power, about 10.5 volts of power, about 11 volts of power, about 11.5 volts of power, about 12 volts of power, about 12.5 volts of power, about 13 volts of power, about 13.5 volts of power, about 14 volts of power, about 14.5 volts of power, between about 9 volts of power and about 13.5 volts of power, between about 9 volts of power to about 13 volts of power, between about 9 volts of power to about 12 volts of power, or between about 9 volts of power to about 11 volts of power. In other embodiments, a battery can provide two voltages of power, one of about 9 volts of power to about 13.5 volts of power, and another of about 9 volts to about 12 volts.

Battery life can be about 6 months to 1 year. In some embodiments, the life of the battery can be about 28 days, about 30 days, about 1 month, about 2 months, about 3 months, about 4 months, about 5 months, about 6 months, about 7 months, about 8 months, about 9 months, about 10 months, about 11 months, about 1 year, at least about 1 day, at least about 1 week, at least about 1 month, at least about 6 months, or at least about 1 year.

In some embodiments, the devices can be used once and then discarded; in other words, the devices can be disposable. In other embodiments, the devices can be reusable allowing a single device to sterilize at least about 10, at least about 50, at least about 100, at least about 250, at least about 500, or at least about 1,000 ports using a single battery. In some embodiments, devices can be discarded after battery depletion. In other embodiments, a battery can be replaced and the device can be used again. In still other embodiments, the battery can be re-charged and the device used again and again. This great number of disinfections using a single device can save cost because one device can sterilize numerous instruments.

The devices can be washable and sterilizable using conventional sterilization techniques. In some embodiments, the devices are sealed sufficiently to allow multiple washings with a detergent or alcohol based cleaner without damaging the device. Further, the devices can be sterilized using gamma irradiation techniques.

In some embodiments, the devices can automatically shut off when the battery is below the threshold to produce enough energy to sterilize the intended surface. This automatic shut off can prevent a device from not completing a sterilization.

In some embodiments, the battery can be removed as needed to clean and/or sterilize the device. In other embodiments, the battery can be removed to be replaced. In some embodiments, the battery lasts for the life of the product without replacement.

The optional printed circuit board can include a processor that can execute instructions stored in memory. Instructions can include sterilization times, light intensities, indicator light scenarios, sensor inputs/outputs, and the like.

In other embodiments, the devices described herein can have independent drivers that do not require a processor. In some embodiments, the independent drivers are LED drivers. The LED drivers can use transistors which do not include using a microprocessor.

In some embodiments, the body can include a light source. In some embodiments, the body can include at least one light source, at least two light sources, at least three light sources or more.

The light source can be an incandescent bulb, a halogen bulb, a xenon bulb, a laser, a laser emitting diode, a monochromatic light, or a light emitting diode (LED). In other embodiments, the light source can be anything that will emit ultraviolet light, ultraviolet C light, or a combination thereof.

In some embodiments, the light source can deliver or project light to sterilize a connection port at the adapter. In some embodiments, the light is ultraviolet light. In some embodiments, the light is ultraviolet C (UVC) light. The light can be delivered from about a 3.5 mm×3.5 mm LED. In other embodiments, the LED can be about 0.5 mm×0.5 mm, about 0.5 mm×1.0 mm, about 1.0 mm×1.0 mm, about 1.5 mm×2.5 mm, about 2.0 mm×2.0 mm, about 2.5 mm×3.5 mm, about 3.0 mm×3.0 mm, about 3.5 mm×4.5 mm, about 4.0 mm×4.0 mm, about 4.5 mm×5.5 mm, or about 5.0 mm×5.0 mm.

In some embodiments, the LED driver can operate at a constant current over the device as the battery degrades. The optical power will degrade, but will remain the same.

In other, embodiments there can be LED modulation. LED modulation can be 10 rbw, 20 rbw, 30 rbw, 40 rbw, 50 rbw, at least 10 rbw, at least 20 rbw, at least 30 rbw, at least 40 rbw, at least 50 rbw, or between 15 rbw and 35 rbw. In some embodiments, there is no LED modulation but rather the devices described herein can operate using constant current mode. In other embodiments, whether the device is using constant power, constant current, or LED modulation, it can be dependent on the life of the battery. In some embodiments, the LED drivers can operate at constant current, constant power, and/or LED modulation.

In some embodiments, UVC light can be delivered with a wavelength of about 100 nm, about 105 nm, about 110 nm, about 115 nm, about 120 nm, about 125 nm, about 130 nm, about 135 nm, about 140 nm, about 145 nm, about 150 nm, about 155 nm, about 160 nm, about 165 nm, about 170 nm, about 175 nm, about 180 nm, about 185 nm, about 190 nm, about 195 nm, about 200 nm, about 205 nm, about 210 nm, about 215 nm, about 220 nm, about 225, nm, about 230 nm, about 235 nm, about 240 nm, about 245 nm, about 250 nm, about 255 nm, about 260 nm, about 265 nm, about 270 nm, about 275 nm, about 280 nm, between about 100 nm to about 160 nm, between about 160 nm to about 210 nm, between about 210 nm to about 260 nm, or between about 220 nm to about 280 nm. In some embodiments, UVC light can be delivered with a wavelength of about 275 nm.

The higher the wavelength utilized, the less energy that is expelled allowing for the devices to be more efficient.

In other embodiments, UVB light can be delivered with a wavelength of about 280 nm, about 285 nm, about 290 nm, about 295 nm, about 300 nm, about 305 nm, about 310 nm, about 315 nm, between about 280 nm to about 300 nm, or between about 285 nm to about 315 nm.

In some embodiments, UV light, B or C, can be delivered for less than about a 5 sec or less than about 10 sec. In some embodiments, light is delivered for between about 5 sec and about 10 sec. In other embodiments, UV light, B or C, can be delivered within about 1 sec, about 2 sec, about 3 sec, about 4 sec, about 5 sec, about 6 sec, about 7 sec, about 8 sec, about 9 sec, about 10 sec, about 11 sec, about 12 sec, about 13 sec, about 14 sec, about 15 sec, about 16 sec, about 17 sec, about 18 sec, about 19 sec, about 20 sec, about 21 sec, about 22 sec, about 23 sec, about 24 sec, about 25 sec, about 26 sec, about 27 sec, about 28 sec, about 29 sec, about 30 sec, about 31 sec, about 31 sec, about 32 sec, about 33 sec, about 34 sec, about 35 sec, about 36 sec, about 37 sec, about 38 sec, about 39 sec, about 40 sec, about 41 sec, about 42 sec, about 43 sec, about 44 sec, about 45 sec, about 46 sec, about 47 sec, about 48 sec, about 49 sec, about 50 sec, about 51 sec, about 52 sec, about 53 sec, about 54 sec, about 55 sec, about 56 sec, about 57 sec, about 58 sec, about 59 sec, about 60 sec, or about one minute.

In some embodiments, UV light, B or C, can be delivered for less than about 1 sec, less than about 2 sec, less than about 3 sec, less than about 4 sec, less than about 5 sec, less than about 6 sec, less than about 7 sec, less than about 8 sec, less than about 9 sec, less than about 10 sec, less than about 11 sec, less than about 12 sec, less than about 13 sec, less than about 14 sec, less than about 15 sec, less than about 16 sec, less than about 17 sec, less than about 18 sec, less than about 19 sec, less than about 20 sec, less than about 21 sec, less than about 22 sec, less than about 23 sec, less than about 24 sec, less than about 25 sec, less than about 26 sec, less than about 27 sec, less than about 28 sec, less than about 29 sec, less than about 30 sec, less than about 31 sec, less than about 32 sec, less than about 33 sec, less than about 34 sec, less than bout 35 sec, less than about 36 sec, less than about 37 sec, less than about 38 sec, less than about 39 sec, less than about 40 sec, less than about 41 sec, less than about 42 sec, less than about 43 sec, less than about 44 sec, less than about 45 sec, less than about 46 sec, less than about 47 sec, less than about 48 sec, less about 49 sec, less than about 50 sec, less than about 51 sec, less than about 52 sec, less than about 53 sec, less than about 54 sec, less than about 55 sec, less than about 56 sec, less than about 57 sec, less than about 58 sec, less than about 59 sec, less than about 60 sec, or less than about one minute.

In some embodiments, UV light, B or C, can be delivered for more than about 1 sec, more than about 2 sec, more than about 3 sec, more than about 4 sec, more than about 5 sec, more than about 6 sec, more than about 7 sec, more than about 8 sec, more than about 9 sec, more than about 10 sec, more than about 11 sec, more than about 12 sec, more than about 13 sec, more than about 14 sec, more than about 15 sec, more than about 16 sec, more than about 17 sec, more than about 18 sec, more than about 19 sec, more than about 20 sec, more than about 21 sec, more than about 22 sec, more than about 23 sec, more than about 24 sec, more than about 25 sec, more than about 26 sec, more than about 27 sec, more than about 28 sec, more than about 29 sec, more than about 30 sec, more than about 31 sec, more than about 32 sec, more than about 33 sec, more than about 34 sec, more than about 35 sec, more than about 36 sec, more than about 37 sec, more than about 38 sec, more than about 39 sec, more than about 40 sec, more than about 41 sec, more than about 42 sec, more than about 43 sec, more than about 44 sec, more than about 45 sec, more than about 46 sec, more than about 47 sec, more than about 48 sec, more than about 49 sec, more than about 50 sec, more than about 51 sec, more than about 52 sec, more than about 53 sec, more than about 54 sec, more than about 55 sec, more than about 56 sec, more than about 57 sec, more than about 58 sec, more than about 59 sec, more than about 60 sec, more than about one minute, between about 0.1 sec to about 5 sec, between about 2 sec to about 3 sec, between about 5 sec to about 7 sec, between about 5 sec to about 10 sec, between about 5 sec to about 11 sec, between about 6 sec to about 12 sec, between about 11 sec to about 15 sec, between about 13 sec to about 25 sec, between about 15 sec to about 30 sec, between about 25 sec to about 35 sec, between about 25 sec to about 45 sec, or between about 25 sec to about 60 sec.

In accordance with signal processing, in some embodiments the pulsed light applied can be a square signal, a rectangular signal, a cosine squared signal, a Dirac signal, a sinc signal, a Gaussian signal, or a combination thereof.

In some embodiments, the device can deliver ultraviolet C (UVC) light to sterilize a connection port. In one embodiment, the UVC light can be delivered from a light source having a size of about 3.5 mm×3.5 mm with a wavelength of about 275 nm for an interval of about 5 sec to about 10 sec at an optical power of about 10 mW to about 50 mW. In another embodiment, the UVC light can be delivered from a light source having a size of about 3.5 mm×3.5 mm with a wavelength of about 275 nm for an interval of less than about 5 sec at an optical power of about 10 mW to about 50 mW. In another embodiment, the UVC light can be delivered from a light source having a size of about 3.5 mm×3.5 mm with a wavelength of about 275 nm for an interval of less than about 10 sec at an optical power of about 10 mW to about 50 mW.

The described light delivery can effectively denature any microbe or cellular structure on the surface of the connection port or surface(s) of an instrument(s).

In some embodiments the optical power can be about 1 mW, about 2 mW, about 3 mW, about 4 mW, about 5 mW, about 6 mW, about 7 mW, about 8 mW, about 9 mW, about 10 mW, about 11 mW, about 12 mW, about 13 mW, about 14 mW, about 15 mW, about 16 mW, about 17 mW, about 18 mW, about 19 mW, about 20 mw, about 25 mW, about 30 mw, between about 1 mW to about 5 mW, between about 1 mW to about 10 mW, between about 5 mW to about 10 mW, between about 5 mW to about 15 mW, between about 10 mW to about 15 mW, between about 10 mW to about 20 mW, or between about 10 mW to about 30 mW. In some embodiments, the optical power can be about 10 mW. In other embodiments, the optical power can be at least 6 mW.

One or more lens is used in conjunction with the light source to focus the light onto the adapter. The one or more lens can be made of plastics or glass or may be formed of a transparent polymer used to make the housing. The lenses can be made to provide a particular focal length to the light. In some embodiments, curvature of the inner or outer surface of the lens, thickness of the lens, refractive index of the lens and the like can be used to provide a particular focal length. In some embodiments, focal length is generally from the light source to the adapter. In other embodiments, the one or more lens can be a conical lens. The conical lens can be a lens with a surface that is a cone instead of the usual sphere. In some embodiments, the conical lens can be used to transform collimated light into a ring to create an approximation of a Bessel beam. In some embodiments, the one or more lens can be a conical TOPAS® lens. In other embodiments, the conical lens can reduce the time frame to focus promoting time efficiency.

In some embodiments, the light source can be at a focal length or distance from the adapter. In some embodiments, the distance can be about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, less than about 1 mm, less than about 2 mm, less than about 3 mm, less than about 4 mm, less than about 5 mm, less than about 6 mm, less than about 7 mm, less than about 8 mm, less than about 9 mm, less than about 10 mm, less than about 11 mm, less than about 12 mm, less than about 13 mm, less than about 14 mm, less than about 15 mm, less than about 16 mm, less than about 17 mm, less than about 18 mm, less than about 19 mm, less than about 20 mm, more than about 1 mm, more than about 2 mm, more than about 3 mm, more than about 4 mm, more than about 5 mm, more than about 6 mm, more than about 7 mm, more than about 8 mm, more than about 9 mm, a more than bout 10 mm, more than about 11 mm, more than about 12 mm, more than about 13 mm, more than about 14 mm, more than about 15 mm, more than about 16 mm, more than about 17 mm, more than about 18 mm, more than about 19 mm, more than about 20 mm, between about 1 mm about 5 mm, between about 5 mm and about 10 mm, between about 7 mm and about 10 mm, between about 5 mm and about 15 mm, between about 8 mm and about 15 mm, or between about 14 mm and about 20 mm. Distance 124 can be between about 5 mm to about 10 mm from the intended surface.

In some embodiments, the light output homogeneity can be characterized such that all areas of the intended surface to be sterilized receive enough exposure. In other embodiments, the least amount of light output can result in an acceptable amount of radiation to sterilize the intended surface. The optical power of the light output homogeneity can be about 6 mW, about 7 mW, about 8 mW, about 9 mW, about 10 mW, at least about 6 mW, at least about 7 mW, at least about 8 mW, at least about 9 mW, at least about 10 mW, more than about 6 mW, more than about 7 mW, more about 8 mW, more than about 9 mW, more than about 10 mW, less than about 6 mW, less than about 7 mW, less than about 8 mW, less than about 9 mW, less than about 10 mW, between about 6 mW to about 10 mW, between about 7 mW to about 9 mW, between about 7 mW to about 8 mW, or about 8 mW to about 9 mW.

In some embodiments, the devices are handheld. In some embodiments, the devices are ergonomic. The devices can be disposable and used for a single use. In other embodiments, the devices can be used multiple times.

In some embodiments, a port cap can be provided to connect to a connection port to keep it sterile until it is hooked and/or used.

In other embodiments, the devices described herein can include an inter-locking circuit. The inter-locking circuit can be a safety feature which can prevent the UV light from being emitted prematurely. In some embodiments, the inter-locking circuit can be an inter-locking circuit cap which is connected to the device. When the inter-locking circuit cap is connected to the device, the safety aspect prevents the UV light from being emitted prematurely.

In other embodiments, the inter-locking circuit can be connected to the adaptor or to a luer to turn on the safety feature. In other embodiments, the inter-locking circuit can have an RFID chip or an optical senor configured to allow the inter-locking circuit cap and device to communicate. In some embodiments, the inter-locking safety feature can be triggered when the inter-locking circuit cap can be connected to the device and the inter-locking circuit cap and RFID/optical sensor can communicate. In some embodiments, the adaptor cap and device can communicate via physical, mechanical, or optical communication.

Using the present devices during surgery can save time and provide a better working environment. It is not uncommon for a surgeon to be wearing several layers of clothing along with surgical barriers, including gloves, face barriers, goggles, hats, and overcoats, to name a few, during a given surgical procedure, contributing to discomfort and fatigue normally associated with hot and bright surgical working environments. The devices described herein provide specific advantages for patient and physician comfort as well as to a surgeon's stamina by decreasing the time of a procedure and/or the time a patient is under anesthesia.

Compounding matters, the complexity of contemporary operating rooms has increased over the years as a result of the extra equipment, fixtures, associated power cords and the like required for ever more complicated surgeries. Such situations are not conducive to comfortable, non-fatiguing surgical environments. The ease of use of the presently described devices and can address and assist in overcoming these issues.

Patient comfort during a surgical procedure is very important, especially when the patient is under local anesthesia and is conscious. It is not uncommon for bright lights to be focused on at least a portion of a patient, typically on the target surgical site. Such lighting systems can get hot and make a patient uncomfortable. Patients who are uncomfortable commonly are more on edge, squirm and/or twitch, or are tense. These are not ideal situations for a patient undergoing surgery. The present lighting device's ability to adequately illuminate a surgical site without the need to direct high intensity lighting during use can simplify and shorten a medical procedure, provide enhanced patient comfort and compliance, and improve the medical procedure's outcome; all while providing the surgeon with enhanced visual control of the process.

Methods are also described for using the herein described devices. A user attaches the adapter to the device. The user starts the device by activating the switch. A light indicates that the device is sterilizing the adapter and then changes color when the cycle is complete.

In another embodiment, a user attaches the adapter to a connection port on an IV line. The adapter inserted into the device, and the device automatically activates and begins to sterilize the surface(s) of the instrument(s). A light indicates when the instrument(s) is sterilized.

In some embodiments, the methods can include connecting the devices to several various fixtures and sterilizing them sequentially one at a time. Such a mass sterilization can take about 30 to about 40 seconds.

In some embodiments, sterilization can be less than 10 minutes, less than 5 minutes, or less than one minute.

In other embodiments, a device can include multiple sterilization adapters to sterilize multiple instruments at one time.

In some embodiments, the device can be prepackaged so there is no gap in exposure time. For example, the device and the adaptor can be prepackaged for a single use. In other embodiments, the device can be prepackaged and the adapter can be separately packaged. The adaptor can be disposable and for a single use.

In some embodiments, kits including the herein described devices can be provided. In one embodiment, a kit can include a device, as described herein, in an appropriate packaging and instructions for use.

In one embodiment, a kit can include a disposable device such as a device, as described herein, in an appropriate packaging and instructions for use.

In one embodiment, a kit can include a device such as a device described herein in an appropriate packaging, a recharging cradle, and instructions for use.

In other embodiments, the very top and lowest shells can be dark by design to contain any and all UV radiation inside. This can be accomplished by the use of sensors and switches such that UV lights turn on only when the system is closed and sealed.

In the example below, an endoscope is being disinfected/sterilized. This process happens after cleaning.

The inner shells (surrounding the endoscope in this case) are made of a UVC transmissible material such as TOPAS or other UVC transparent materials. These inner shells with the outer shells also control the spacing from the UVC LEDS such that all exposed areas on the subject device (endoscope in this case as shown) receive enough radiant energy to achieve the required dose of energy to result in the required level of disinfection/sterilization.

The number of UVC LEDs, light emitting diodes, may be different of any given device. In some cases, if the instrument has a lumen that is required to be disinfected/sterilized, a light pipe or other mechanism can be used.

The device can include a screen display. This incorporated a GUI, graphical user interface, to provide control and feedback to the user.

The device can include "drawers" or "cabinets" to make the insertion/removal of the given device more user friendly.

The device can have multiple "drawers" or "cabinets" to perform cycles on multiple devices.

The drawers or cabinets can stack, slide or be connected by a hinge.

The device can incorporate a microprocessor and sensors to perform the above.

The device may be a system and may also beep to provide auditory feedback to the user.

Example 1

The devices as described herein, were used to test the efficacy of killing methicillin-resistant *Staphylococcus aureus* (MRSA) on IV connector surfaces after 1 second, after 3 seconds, and after 7 seconds of exposure time.

Culture Preparation

MRSA was plated onto tryptic soy agar supplemented with 5% sheep blood (TSAB) and incubated at 35° C. for 24 hours. Well isolated colonies were transferred into phosphate buffer water (PBW) and adjusted to approximately $1 \times 10^8$ CFU/mL before the testing was conducted. The inoculum was used to contaminate the septum surfaces of IV connectors.

Quantitative Testing

Each test surface was inoculated with 50 μL of the inoculum and left to air dry for 4 hours at ambient temperature inside a biological safety cabinet. Inoculated test surfaces were individually placed into UV devices and subjected to one second, three seconds, and seven seconds of exposure to the UV light. Three untreated test surfaces were used as controls to determine starting population size of the inoculum. All tests were performed in triplicate. Remaining bacteria were recovered from the test surfaces by washing the surfaces 8 times using neutralizing solution and PBW and plated onto HardyCHROM *Staph aureus* agar.

Untreated-controls of bacterial cultures were serially diluted and plated using AC Petrifilm and incubated at 35° C. for 48 hrs. Colonies were counted following incubation and used to calculate percent reduction (efficacy) of UV light against the test bacteria.

TABLE 1

MRSA colony forming units (CFU) on test surfaces with and without UV exposure in the UV device.

| UV Exposure | Test Avg. CFU/Test Surface (average of 3 tests) | Log | Log Reduction | % Reduction |
| --- | --- | --- | --- | --- |
| Control (untreated) | 8,233,333 | 6.916 | | |
| 1 sec UV | 300 | 2.478 | 4.44 | 99.996 |
| 3 sec UV | 30 | 1.472 | 5.44 | 99.996 |
| 7 sec UV | <1 | 0.000 | 6.92 | >99.99999 |

CFU: Conly Forming Unites, Detection Limit = 1CFU;
% Reduction - Percent difference between untreated population The devices described herein can reduce MSRA bacteria on IV connectors with 99.99% kill after 1 second, 99.999% kill after 3 seconds, and >99.99999% after 7 seconds of UV treatment. These results demonstrate the effectiveness of the devices described herein. In comparison, current methods on the market take days to reach only a 98% kill, whereas the devices described herein take a second to achieve a 99.99% kill.

The experimental results show 99.99% kill after 1 second of UV light exposure (where the bacterial growth was after 48 hours of incubation), 99.996% kill after 3 seconds of UV light exposure (where the bacterial growth was after 48 hours of incubation), and >99.99999% kill after 7 seconds of UV light exposure (where the bacterial growth was after 48 hours of incubation).

Example 2

Sterilization of IV Connection Ports

Post surgery a patient is in a recovery room and is connected to three IV bags. The IV bags need to be changed. A medical professional comes in and removes the bags. Prior to attaching new bags, the medical professional uses the devices described herein to sterilize the surface of the connection ports. The medical professional inserts the device into one/the first connection port and switches on the device. The LED indicator lights start illuminating red incrementally. After about five seconds the red LED indicator lights turn green. The green LED indicator lights signal to the medical professional that surface of the connection port is sterilized. The medical professional then attaches the new bag. Then using the same procedure the medical professional sterilizes the remaining two connection ports and attaches the new bags. The IV bag change is then complete.

Example 3

Sterilization of IV Connection Ports 2

Post surgery a patient is in a recovery room and is connected to three IV bags. The IV bags need to be changed. A medical professional comes in and removes the bags. Prior to attaching new bags, the medical professional uses the devices described herein to sterilize the surface of the connection ports. The medical professional inserts the device into one/the first connection port and switches on the device. The LED indicator lights start illuminating red incrementally. After about five seconds the red LED indicator lights turn off, and the LED indicator lights turn green. The green LED indicator lights signal to the medical professional that surface of the connection port is sterilized. The medical professional attaches a sterile port cap to the connection port to keep it sterile while she sterilizes the remaining connection ports. After the sterilization of each connection port she connects a sterile port cap to the connection port. Once the medical professional has completed sterilizing all the connection ports she begins hooking up the new bags. She first removes one port cap and hooks up the new bag. This is repeated until are three bags are up. The IV bag change is then complete.

Example 4

Post surgery a patient is in a recovery room and is connected to three IV bags. The IV bags need to be changed. A medical professional comes in, but is called out due to an emergency. Thus, the medical professional connects an inter-locking circuit cap to the devices described herein. The inter-locking circuit cap is connected to the device as a safety feature while the medical professional leaves the room to attend to the emergency. The inter-locking circuit cap prevents the UV light from being emitted prematurely. The inter-locking circuit cap has an RFID chip configured to allow the inter-locking circuit cap and device to communicate once the inter-locking circuit cap is connected to the devices described herein.

After the emergency is over the medical professional comes back into the patient's recovery room. The medical professional now removes the bags. Prior to attaching new bags, the medical professional uses the devices described herein to sterilize the surface of the connection ports. The medical professional removes the inter-locking circuit cap, thus removing the safety feature. Then, the medical professional inserts the device into one/the first connection port and switches on the device. The LED indicator lights start illuminating red incrementally. After about five seconds the red LED indicator lights turn off, and the LED indicator lights turn green. The green LED indicator lights signal to the medical professional that surface of the connection port is sterilized. The medical professional attaches a sterile port cap to the connection port to keep it sterile while she sterilizes the remaining connection ports. After the sterilization of each connection port she connects a sterile port cap to the connection port. Once the medical professional has completed sterilizing all the connection ports she begins hooking up the new bags. She first removes one port cap and hooks up the new bag. This is repeated until are three bags are up. The IV bag change is then complete.

Example 5

MRSA is plated onto twelve tryptic soy agar plates and incubated for 48 hours. Three of the plates are used as controls. The remaining plates were individually placed into UV devices and subjected to one second, three second, and seven seconds of exposure to UV light. All tests were performed in triplicate.

Example 6

A surgical procedure is taking place and a surgical instrument or tool is requested by the surgeon for a specific dissection maneuver. If this specific instrument has not been previously sterilized and prepared for the procedure ahead of time this may put the surgeon in a compromising position potentially with the patients' life at risk.

The staff could utilize the device and adapter to quickly and conveniently sterilize the instrument or set of instruments in the operating room area. After the UV irradiation cycle is complete, which could be a matter of seconds or minutes, the instrument can then be safely handed off or delivered to the surgeon or scrub tech using a sterile technique. The surgeon can then utilize the instrument to perform a life saving operation or routine surgical technique.

The plates exposed to 1 second of UV light exposure had a 99.99% kill. The plates exposed to 3 seconds of UV light exposure had a 99.996% kill. The plates exposed to 7 seconds of UV light exposure had a >99.99999% kill.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A sterilization device comprising:
    a body comprising at least one indicator light, a power source, and at least one light source; and
    an adapter comprising a lens and a substrate configured to provide a color change;
    wherein the adapter is a shell configured to enclose an instrument for sterilization.

2. The sterilization device of claim 1, wherein the power source is at least 3 volts.

3. The sterilization device of claim 1, wherein the at least one indicator light turns green after the instrument is sterilized.

4. The sterilization device of claim 1, wherein the at least one light source is a light emitting diode.

5. The sterilization device of claim 1, wherein the at least one light source is a laser emitting diode.

6. The sterilization device of claim 1, wherein the at least one light source emits ultraviolet C light.

7. The sterilization device of claim 1, wherein the at least one light source has a wavelength of about 275 nm.

8. The sterilization device of claim 1, wherein the at least one light source has an optical power of about 30 mW.

9. The sterilization device of claim 1, wherein the adapter is sterile.

10. The sterilization device of claim 1, wherein the adapter is disposable.

11. The sterilization device of claim 1, further including a switch, at least one or more sensors, or a multi-sensor to activate the sterilization device.

12. The sterilization device of claim 1, wherein sterilization occurs in less than about 10 minutes.

13. The sterilization device of claim 1, wherein sterilization occurs in less than about 10 sec.

14. The sterilization device of claim 1, wherein microbial reduction is a 7-log microbial reduction.

* * * * *